(12) United States Patent
Cai

(10) Patent No.: US 11,766,114 B2
(45) Date of Patent: Sep. 26, 2023

(54) METHOD FOR PREPARING POROUS ANTIBACTERIAL FIBER BRUSH

(71) Applicant: GUANGDONG NEWDERMO BIOTECH CO., LTD, Guangzhou (CN)

(72) Inventor: Qingyao Cai, Guangzhou (CN)

(73) Assignee: GUANGDONG NEWDERMO BIOTECH CO., LTD, Guangzhou (CN)

( * ) Notice: Subject to any disclaimer, the term of this patent is extended or adjusted under 35 U.S.C. 154(b) by 569 days.

(21) Appl. No.: 17/039,993

(22) Filed: Sep. 30, 2020

(65) Prior Publication Data

US 2021/0315374 A1    Oct. 14, 2021

(30) Foreign Application Priority Data

Apr. 14, 2020   (CN) .......................... 202010292299.8

(51) Int. Cl.
  *A46D 1/00*    (2006.01)
  *A46D 1/06*    (2006.01)
  *A46D 1/045*   (2006.01)
  *A61K 8/19*    (2006.01)

(52) U.S. Cl.
  CPC .............. *A46D 1/006* (2013.01); *A46D 1/045* (2013.01); *A46D 1/06* (2013.01); *A61K 8/19* (2013.01)

(58) Field of Classification Search
  CPC .................................. A46D 1/045; A46D 1/006
  USPC ......................................................... 156/73.2
  See application file for complete search history.

(56) References Cited

PUBLICATIONS

Clarivate Analytics (PE2E search) Machine-translation of CN-101909485-B (Honnefeller K., CN, A46B3/20, Nov. 2012); with its foreign patent attached. (Year: 2012).*
Clarivate Analytics (PE2E search) Machine-translation of JP-2002330824-A (Kobayashi K., JP, A46D1/06, Nov. 2002); with its foreign patent attached. (Year: 2002).*
Clarivate Analytics (PE2E search) Machine-translation of CN-105407759-A (Kim L S., CN, A46B7/04, Mar. 2016); with its foreign patent attached. (Year: 2016).*
Clarivate Analytics (PE2E search) Machine-translation of WO-2014014038-A1 (Oue K., WO, A46B15/0026, Jan. 2014); with its foreign patent attached. (Year: 2014).*

* cited by examiner

*Primary Examiner* — Matthew J Daniels
*Assistant Examiner* — Gregory C. Grosso

(57) ABSTRACT

The present disclosure provides a method for preparing a porous antibacterial fiber brush. Fiber masterbatch made of ultra-fine reaming silica gel, silver-based antibacterial agent and other materials is melted, drawn, cut, polished and then dried to make the porous antibacterial fiber brush. A large number of micropores are distributed on the surface of the porous antibacterial fiber brush, which absorb cosmetic residues on the skin surface and tiny dirt in the pores, and realize efficient cleaning of the surface of human skin.

10 Claims, No Drawings

METHOD FOR PREPARING POROUS ANTIBACTERIAL FIBER BRUSH

CROSS REFERENCE TO RELATED APPLICATIONS

The present application claims the benefit of Chinese Patent Application No. 202010292299.8 filed on Apr. 14, 2020, the contents of which are incorporated herein by reference in their entirety.

TECHNICAL FIELD

The present disclosure relates to a field of brush production technology, and in particular to a method for preparing a porous antibacterial fiber brush.

BACKGROUND ART

The skin dirt on the surface of the human body is mainly inorganic salt, oil, bacteria, waste cutin, etc. In addition, cosmetic residues also easily cause clogging of pores and cause skin damage. People's daily cleaning only removes oil on the surface of the skin, and even if a common cleansing brush or other skin cleaning equipment are used, they are unable to effectively clean the pores.

Porous fiber material refers to a material with a network structure composed of interpenetrating pores or closed pores. Porous fiber materials have broad application prospects in biomedicine, tissue scaffolds, battery diaphragms, air filtration and sensors, etc. due to the size effect of multiple micropores.

At present, there is no case in the prior art where porous fiber material applied to a field of high-efficiency cleansing of human skin.

SUMMARY OF THE INVENTION

An object of the present disclosure is to provide a method for preparing a porous antibacterial fiber brush to solve a technical problem mentioned above.

To achieve the above object, the present disclosure provides a method for preparing a porous antibacterial fiber brush. The method comprises following steps:
  melting and drawing fiber masterbatch and cutting the fiber masterbatch into short fibers; wherein the fiber masterbatch comprises following raw materials by weight: ultra-fine reaming silica gel provided in an amount ranging from 10-30%, silane coupling agent provided in an amount ranging from 0.5-5%, silver-based antibacterial agent provided in an amount ranging from 0.1-2%, pigment provided in an amount ranging from 0-1%, and thermoplastic polymer provided in balance; wherein the thermoplastic polymer is selected from any one or two of polybutylene terephthalate and polyamide.
  uniformly polishing top ends of the short fibers at a temperature ranging from −20° C. to −40° C.;
  ultrasonic cleaning the short fibers and vacuum drying the short fibers; and
  transplanting the short fibers on a head of a brush to obtain the porous antibacterial fiber brush.

Furthermore, the fiber masterbatch is prepared by:
  separately drying the thermoplastic polymer and the ultra-fine reaming silica gel;
  uniformly mixing the thermoplastic polymer and the ultra-fine reaming silica gel and then adding and mixing the silver-based antibacterial agent and the pigment to form a mixture; and then mixing and extruding the mixture at a temperature ranging from 230-260° C.;
  putting the mixture into a crushing granulator after the mixture is cooled; crushing and granulating the mixture; and
  drying the mixture to obtain the fiber masterbatch Furthermore, the thermoplastic polymer and the ultra-fine reaming silica gel are separately dried at a temperature ranging from 120-150° C. for 5-10 hours.

Furthermore, the mixture after crushing and granulating is dried at a temperature ranging from 100-120° C. for 8-12 hours.

Furthermore, when cumulative particle size distribution percentage of the ultra-fine reaming silica gel reaches 50%, a corresponding particle size of the ultra-fine reaming silica gel is 1-10 μm, and a pore size of the ultra-fine reaming silica gel ranges from 10-200 nm.

Furthermore, the step of uniformly polishing top ends of the short fibers at the temperature ranging from −20° C. to −40° C. comprises steps:
  freezing the short fibers at the temperature ranging from −20° C. to −40° C. for 0.5-1 hours,
  fixing the short fibers on a spindle of a polishing machine; and
  turning on the polishing machine and polishing the top ends of the short fibers for two times by a rotating polishing disk;
  wherein when polishing, each short fiber uniformly contacts the rotating polishing disk each time.

Furthermore, a polishing direction of the short fibers for a first time is opposite to a polishing direction of the short fibers for a second time. A time of each polishing of the short fibers ranges from 1-5 minutes.

Furthermore, a rotating speed of the polishing disk ranges from 100-500 rpm.

Furthermore, the short fibers contact the rotating polishing disk at a uniform speed of 0.5-2 mm/min.

Furthermore, a diameter of each short fiber of the porous antibacterial fiber brush ranges from 20~200 μm. The top ends of the short fibers have no shearing edges. A surface of each short fiber comprises a large amount of micropores. A pore size of each micropore ranges from 10-20 nm.

In the present disclosure, the fiber masterbatch is made of the ultra-fine reaming silica gel, the silver-based antibacterial agent and other materials. And the fiber masterbatch is melted, drawn, cut, polished and then dried to make a brush. A large number of micropores are distributed on the surface of the brush, which absorb cosmetic residues on the skin surface and tiny dirt in the pores, and realize efficient cleaning of the surface of human skin. The fiber masterbatch comprises silver-based antibacterial agent, which reduces the growth of bacteria during use and make the porous antibacterial fiber brush easy to maintain and ensure hygiene of the porous antibacterial fiber brush

DETAILED DESCRIPTION OF EMBODIMENTS

The specific embodiments of the present disclosure will be further described below. It should be noted that the description of these embodiments is used to help understand the present disclosure, but does not intend to limit the present disclosure. In addition, the technical features involved in the various embodiments of the present disclosure described below can be combined with each other as long as they do not conflict with each other.

The silver-based antibacterial agent in the following embodiments is silver ion antibacterial calcium phosphate, or, the silver-based antibacterial agent is selected from any one or more of silver ion antibacterial zeolite, silver ion antibacterial calcium phosphate, silver iodide, and silver sulfadiazine to replace the silver ion antibacterial calcium phosphate.

Embodiment 1

The present disclosure provides a method for preparing a porous antibacterial fiber brush, comprises following steps:
(1) weighing following raw materials by weight: ultra-fine reaming silica gel provided in an amount of 20% (where a particle size D50 of the ultra-fine reaming silica gel ranges from 5~6 μm, and a pore size of the ultra-fine reaming silica gel ranges from 10~20 nm); silane coupling agent provided in an amount of 3%, silver-based antibacterial agent provided in an amount of 0.5%, and polybutylene terephthalate provided in an amount of 76.5%; separately drying the polybutylene terephthalate and the ultra-fine reaming silica gel at a temperature of 150° C. for 5 hours; uniformly mixing the dried ultra-fine reaming silica gel and the silane coupling agent, and then adding and mixing the silver-based antibacterial agent to form a mixture; and then mixing and extruding the mixture at a temperature ranging from 230-260° C.; putting the mixture into a crushing granulator after the mixture is cooled; crushing and granulating the mixture; and drying the mixture at a temperature of 120° C. for 10 hours to obtain the fiber masterbatch;
(2) melting and drawing fiber masterbatch and cutting the fiber masterbatch into short fibers;
(3) freezing the short fibers at −30° C. for 1 hour, fixing the short fibers on a spindle of a polishing machine at −30° C.; and turning on the polishing machine and polishing the top ends of the short fibers two times by a rotating polishing disk;
(4) ultrasonic cleaning the polished short fibers and vacuum drying the short fibers at a temperature of 50° C.; and
(5) transplanting the short fibers on a head of a brush to obtain the porous antibacterial fiber brush.

When polishing, short fibers uniformly contact the rotating polishing disk each time at a speed of 1 mm/min. A polishing direction of the short fibers for a first time is opposite to a polishing direction of the short fibers for a second time. A time of each polishing of the short fibers is 2 minutes. A rotating speed of the polishing disk is 300 rpm.

It can be seen by electron microscopy that a diameter of each short fiber of the porous antibacterial fiber brush of the embodiment is 50 μm. The top ends of the short fibers have no shearing edges, and a surface of each short fiber comprises a large amount of micropores. A pore size of each micropore ranges from 10-20 nm.

The porous antibacterial fiber brush of the embodiment is able to efficiently remove cosmetic residues on a surface of human skin. A detection rate of cosmetic residues of the porous antibacterial fiber brush after using is no more than 1% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 2%.

Embodiment 2

The present disclosure provides a method for preparing a porous antibacterial fiber brush, comprises following steps:
(1) weighing following raw materials by weight: ultra-fine reaming silica gel provided in an amount of 15% (where a particle size D50 of the ultra-fine reaming silica gel ranges from 5~6 μm, and a pore size of the ultra-fine reaming silica gel ranges from 100~200); silane coupling agent provided in an amount of 2.5%, silver-based antibacterial agent provided in an amount of 1%, pigment provided in an amount ranging from 0-1%, and polyamide provided in an amount of 81.5%; separately drying the polyamide and the ultra-fine reaming silica gel at a temperature of 150° C. for 5 hours; uniformly mixing the dried ultra-fine reaming silica gel and the silane coupling agent, and then adding and mixing the silver-based antibacterial agent and the pigment to form a mixture; and then mixing and extruding the mixture at a temperature ranging from 230-260° C.; putting the mixture into a crushing granulator after the mixture is cooled; crushing and granulating the mixture; and drying the mixture at a temperature of 120° C. for 10 hours to obtain the fiber masterbatch;
(2) melting and drawing fiber masterbatch and cutting the fiber masterbatch into short fibers;
(3) freezing the short fibers at −30° C. for 1 hour, fixing the short fibers on a spindle of a polishing machine at −30° C.; and turning on the polishing machine and polishing the top ends of the short fibers for two times by a rotating polishing disk;
(4) ultrasonic cleaning the polished short fibers and vacuum drying the short fibers at a temperature of 50° C.; and
(5) transplanting the short fibers on a head of a brush to obtain the porous antibacterial fiber brush.

When polishing, short fibers uniformly contact the rotating polishing disk each time at a speed of 1 mm/min. A polishing direction of the short fibers for a first time is opposite to a polishing direction of the short fibers for a second time. A time of each polishing of the short fibers is 2 minutes. A rotating speed of the polishing disk is 300 rpm.

It can be seen by electron microscopy that a diameter of each short fiber of the porous antibacterial fiber brush of the embodiment is 100 μm. The top ends of the short fibers have no shearing edges, and a surface of each short fiber comprises a large amount of micropores. A pore size of each micropore ranges from 10-20 nm.

The porous antibacterial fiber brush of the embodiment is able to efficiently remove cosmetic residues on a surface of human skin. A detection rate of cosmetic residues of the porous antibacterial fiber brush after using is no more than 1% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 1%.

Embodiment 3

The present disclosure provides a method for preparing a porous antibacterial fiber brush, comprises following steps:

(1) weighing following raw materials by weight: ultra-fine reaming silica gel provided in an amount of 10% (where a particle size D50 of the ultra-fine reaming silica gel ranges from 5~6 μm, and a pore size of the ultra-fine reaming silica gel ranges from 10~20 nm); silane coupling agent provided in an amount of 5%, silver-based antibacterial agent provided in an amount of 0.1%, pigment provided in an amount of 1%, and polybutylene terephthalate provided in balance; separately drying the polybutylene terephthalate and the ultra-fine reaming silica gel at a temperature of 150° C. for 5 hours; uniformly mixing the dried ultra-fine reaming silica gel and the silane coupling agent, and then adding and mixing the silver-based antibacterial agent and the pigment to form a mixture; and then mixing and extruding the mixture at a temperature ranging from 230-260° C.; putting the mixture into a crushing granulator after the mixture is cooled; crushing and granulating the mixture; and drying the mixture at a temperature of 100° C. for 12 hours to obtain the fiber masterbatch;

(2) melting and drawing fiber masterbatch and cutting the fiber masterbatch into short fibers;

(3) freezing the short fibers at −40° C. for 0.5 hour, fixing the short fibers on a spindle of a polishing machine at −40° C.; and turning on the polishing machine and polishing the top ends of the short fibers for two times by a rotating polishing disk;

(4) ultrasonic cleaning the polished short fibers and vacuum drying the short fibers at a temperature of 50° C.; and (5) transplanting the short fibers on a head of a brush to obtain the porous antibacterial fiber brush.

When polishing, short fibers uniformly contact the rotating polishing disk each time at a speed of 0.5 mm/min. A polishing direction of the short fibers for a first time is opposite to a polishing direction of the short fibers for a second time. A time of each polishing of the short fibers is 1 minute. A rotating speed of the polishing disk is 100 rpm.

It can be seen by electron microscopy that a diameter of each short fiber of the porous antibacterial fiber brush of the embodiment is 200 μm. The top ends of the short fibers have no shearing edges, and a surface of each short fiber comprises a large amount of micropores. A pore size of each micropore ranges from 10-20 nm.

The porous antibacterial fiber brush of the embodiment is able to efficiently remove cosmetic residues on a surface of human skin. A detection rate of cosmetic residues of the porous antibacterial fiber brush after using is no more than 8% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 9%.

Embodiment 4

The present disclosure provides a method for preparing a porous antibacterial fiber brush, comprises following steps:

(1) weighing following raw materials by weight: ultra-fine reaming silica gel provided in an amount of 30% (where a particle size D50 of the ultra-fine reaming silica gel ranges from 5~6 μm, and a pore size of the ultra-fine reaming silica gel ranges from 10~20 nm); silane coupling agent provided in an amount of 0.5%, silver-based antibacterial agent provided in an amount of 2%, pigment provided in an amount of 0.5% and polybutylene terephthalate provided in balance; separately drying the polybutylene terephthalate and the ultra-fine reaming silica gel at a temperature of 130° C. for 8 hours; uniformly mixing the dried ultra-fine reaming silica gel and the silane coupling agent, and then adding and mixing the silver-based antibacterial agent and the pigment to form a mixture; and then mixing and extruding the mixture at a temperature ranging from 230-260° C.; putting the mixture into a crushing granulator after the mixture is cooled; crushing and granulating the mixture; and drying the mixture at a temperature of 120° C. for 10 hours to obtain the fiber masterbatch;

(2) melting and drawing fiber masterbatch and cutting the fiber masterbatch into short fibers;

(3) freezing the short fibers at −20° C. for 1 hour, fixing the short fibers on a spindle of a polishing machine at −20° C.; and turning on the polishing machine and polishing the top ends of the short fibers two times by a rotating polishing disk;

(4) ultrasonic cleaning the polished short fibers and vacuum drying the short fibers at a temperature of 50° C.; and (5) transplanting the short fibers on a head of a brush to obtain the porous antibacterial fiber brush.

When polishing, short fibers uniformly contact the rotating polishing disk each time at a speed of 2 mm/min. A polishing direction of the short fibers for a first time is opposite to a polishing direction of the short fibers for a second time. A time of each polishing of the short fibers is 5 minutes. A rotating speed of the polishing disk is 500 rpm.

It can be seen by electron microscopy that a diameter of each short fiber of the porous antibacterial fiber brush of the embodiment is 20 μm. The top ends of the short fibers have no shearing edges, and a surface of each short fiber comprises a large amount of micropores. A pore size of each micropore ranges from 10-20 nm.

The porous antibacterial fiber brush of the embodiment is able to efficiently remove cosmetic residues on a surface of human skin. A detection rate of cosmetic residues of the porous antibacterial fiber brush after using is no more than 5% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 5%.

Embodiment 5

The present disclosure provides a method for preparing a porous antibacterial fiber brush, comprises following steps:

(1) weighing following raw materials by weight: ultra-fine reaming silica gel provided in an amount of 12% (where a particle size D50 of the ultra-fine reaming silica gel ranges from 5~6 μm, and a pore size of the ultra-fine reaming silica gel ranges from 10~20 nm); silane coupling agent provided in an amount of 2%, silver-based antibacterial agent provided in an amount of 1%, pigment provided in an amount of 0.5% and polybutylene terephthalate provided in balance; separately drying the polybutylene terephthalate and the ultra-fine reaming silica gel at a temperature of 140° C. for 8 hours; uniformly mixing the dried ultra-fine reaming silica gel and the silane coupling agent, and then adding and mixing the silver-based antibacterial agent and the pigment to form a mixture; and then mixing and extruding the mixture at 230-260° C.; putting the mixture into a crushing granulator after the mixture is cooled; crushing and granulating the mixture; and drying the mixture at a temperature of 120° C. for 10 hours to obtain the fiber masterbatch;

(2) melting and drawing fiber masterbatch and cutting the fiber masterbatch into short fibers;

(3) freezing the short fibers at −30° C. for 1 hour, fixing the short fibers on a spindle of a polishing machine at −30° C.; and turning on the polishing machine and polishing the top ends of the short fibers two times by a rotating polishing disk;

(4) ultrasonic cleaning the polished short fibers and vacuum drying the short fibers at a temperature of 50° C.; and (5) transplanting the short fibers on a head of a brush to obtain the porous antibacterial fiber brush.

When polishing, short fibers uniformly contact the rotating polishing disk each time at a speed of 1 mm/min. A polishing direction of the short fibers for a first time is opposite to a polishing direction of the short fibers for a second time. A time of each polishing of the short fibers is 2 minutes. A rotating speed of the polishing disk is 300 rpm.

It can be seen by electron microscopy that a diameter of each short fiber of the porous antibacterial fiber brush of the embodiment is 80 µm. The top ends of the short fibers have no shearing edges, and a surface of each short fiber comprises a large amount of micropores. A pore size of each micropore ranges from 10-20 nm. The porous antibacterial fiber brush of the embodiment is able to efficiently remove cosmetic residues on a surface of human skin. A detection rate of cosmetic residues of the porous antibacterial fiber brush after using is no more than 1% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 2%.

Embodiment 6

The present disclosure provides a method for preparing a porous antibacterial fiber brush, comprises following steps:

(1) weighing following raw materials by weight: ultra-fine reaming silica gel provided in an amount of 18% (where a particle size D50 of the ultra-fine reaming silica gel ranges from 5~6 µm, and a pore size of the ultra-fine reaming silica gel ranges from 100~200 nm); silane coupling agent provided in an amount of 3%, silver-based antibacterial agent provided in an amount of 1.2%, pigment provided in an amount of 0.8%, and polyamide provided in balance; separately drying the polyamide and the ultra-fine reaming silica gel at a temperature of 120° C. for 10 hours; uniformly mixing the dried ultra-fine reaming silica gel and the silane coupling agent, and then adding and mixing the silver-based antibacterial agent and the pigment to form a mixture; and then mixing and extruding the mixture at 230-260° C.; putting the mixture into a crushing granulator after the mixture is cooled; crushing and granulating the mixture; and drying the mixture at a temperature of 120° C. for 10 hours to obtain the fiber masterbatch;

(2) melting and drawing fiber masterbatch and cutting the fiber masterbatch into short fibers;

(3) freezing the short fibers at −30° C. for 1 hour, fixing the short fibers on a spindle of a polishing machine at −30° C.; and turning on the polishing machine and polishing the top ends of the short fibers for two times by a rotating polishing disk;

(4) ultrasonic cleaning the polished short fibers and vacuum drying the short fibers at a temperature of 50° C.; and (5) transplanting the short fibers on a head of a brush to obtain the porous antibacterial fiber brush.

When polishing, short fibers uniformly contact the rotating polishing disk each time at a speed of 1 mm/min. A polishing direction of the short fibers for a first time is opposite to a polishing direction of the short fibers for a second time. A time of each polishing of the short fibers is 3 minutes. A rotating speed of the polishing disk is 250 rpm.

It can be seen by electron microscopy that a diameter of each short fiber of the porous antibacterial fiber brush of the embodiment is 70 µm. The top ends of the short fibers have no shearing edges, and a surface of each short fiber comprises a large amount of micropores. A pore size of each micropore ranges from 10-20 nm.

The porous antibacterial fiber brush of the embodiment is able to efficiently remove cosmetic residues on a surface of human skin. A detection rate of cosmetic residues of the porous antibacterial fiber brush after using is no more than 1% (represented by dyes and pigments). The porous antibacterial fiber brush has a soft touch on the skin, and there is no irritation and pain when touching the skin. The porous antibacterial fiber brush also has good antibacterial properties. After ultrasonic cleaning, a detection rate of *E. coli* within 72 hours is no more than 1%.

The above embodiments of the present disclosure have been described in detail, but the described embodiments are not intended to limit the present disclosure. For those skilled in the art, without departing from the principle and spirit of the present disclosure, various changes, modifications, substitutions, and modifications to these embodiments shall still fall within the protection scope of the present disclosure.

The invention claimed is:

1. A method for preparing a porous antibacterial fiber brush, comprising following steps:

melting and drawing fiber masterbatch and cutting the fiber masterbatch into short fibers; wherein the fiber masterbatch comprises following raw materials by fight: ultra-fine reaming silica gel provided in an amount ranging from 10-30%, silane coupling agent provided in an amount ranging from 0.5-5%, silver-based antibacterial agent provided in an amount ranging from 0.1-2%, pigment provided in an amount ranging from 0-1%, and thermoplastic polymer provided in balance; wherein the thermoplastic polymer is selected from any one or two of polybutylene terephthalate and polyamide.

uniformly polishing top ends of the short fibers at a temperature ranging from −20° C. to −40° C.;

ultrasonic cleaning the short fibers and vacuum drying the short fibers; and transplanting the short fibers on a head of a brush to obtain the porous antibacterial fiber brush.

2. The method according to claim 1, wherein the fiber masterbatch is prepared by:

separately drying the thermoplastic polymer and the ultra-fine reaming silica uniformly mixing the thermoplastic polymer and the ultra-fine reaming silica gel and then adding and mixing the silver-based antibacterial agent and the pigment to form a mixture; and then mixing and extruding the mixture at a temperature ranging from 230-260° C.;

putting the mixture into a crushing granulator after the mixture is cooled, crushing and granulating the mixture; and drying mixture to obtain the fiber masterbatch.

3. The method according to claim 2, wherein the thermoplastic polymer and the ultra-fine reaming silica gel are separately dried at a temperature ranging from 120-150° C. for 5-10 hours.

4. The method according to claim 2, wherein the mixture after crushing and granulating is dried at a temperature ranging from 100-120° C. for 8-12 hours.

5. The method according to claim 1, wherein when a cumulative particle size distribution percentage of the ultra-fine reaming silica gel reaches 50%, a corresponding particle size of the ultra-fine reaming silica gel is 1-10 μm, and a pore size of the ultra-fine reaming silica gel ranges from 10-200 nm.

6. The method according to claim 1, wherein the step of uniformly polishing top ends of the short fibers at the temperature ranging from −20° C. to −40° C. comprises steps:

freezing the short fibers at the temperature ranging from 20° C. to −40° C. for 0.5-1 hours, fixing the short fibers on a spindle of a polishing machine; and turning on the polishing machine and polishing the top ends of the short fibers two times by a rotating polishing disk;

wherein when polishing, short fibers uniformly contact the rotating polishing disk each time.

7. The method according to claim 6, wherein a polishing direction of the short fibers for a first time is opposite to a polishing direction of the short fibers for a second time, a time of each polishing of the short fibers ranges from 1-5 minutes.

8. The method according to claim 6, wherein a rotating speed of the polishing disk ranges from 100-500 rpm.

9. The method according to claim 6, wherein the short fibers contact the rotating polishing disk at a uniform speed ranging from 0.5-2 mm/min.

10. The method according to claim 1, wherein a diameter of each short fiber of the porous antibacterial fiber brush ranges from 20-200 μm, the top ends of the short fibers have no shearing edges, and a surface of each short fiber comprises a large amount of micropores, a pore size of each micropore ranges from 10-20 nm.

\* \* \* \* \*